US012427375B2

(12) United States Patent
Russell et al.

(10) Patent No.: US 12,427,375 B2
(45) Date of Patent: Sep. 30, 2025

(54) REAL-TIME, FULLY INTERACTIVE, VIRTUAL SPORTS AND WELLNESS TRAINER AND PHYSIOTHERAPY SYSTEM

(71) Applicant: 4D Health Science LLC, Pinehurst, NC (US)

(72) Inventors: Kim Russell, Pinehurst, NC (US); David Horachek, Pinehurst, NC (US); Eduardo Guendelman, Pinehurst, NC (US); Jochem Hess, Pinehurst, NC (US)

(73) Assignee: 4D Health Science LLC, Pinehurst, NC (US)

( * ) Notice: Subject to any disclaimer, the term of this patent is extended or adjusted under 35 U.S.C. 154(b) by 879 days.

(21) Appl. No.: 17/416,236

(22) PCT Filed: Dec. 18, 2019

(86) PCT No.: PCT/US2019/067242
§ 371 (c)(1),
(2) Date: Jun. 18, 2021

(87) PCT Pub. No.: WO2020/132110
PCT Pub. Date: Jun. 25, 2020

(65) Prior Publication Data
US 2022/0072377 A1 Mar. 10, 2022

Related U.S. Application Data

(60) Provisional application No. 62/781,332, filed on Dec. 18, 2018.

(51) Int. Cl.
*A63B 24/00* (2006.01)
*A63B 71/06* (2006.01)
*G06V 10/25* (2022.01)
*G06V 40/10* (2022.01)
*G06V 40/20* (2022.01)
*G16H 20/30* (2018.01)
*G16H 40/67* (2018.01)

(52) U.S. Cl.
CPC ...... *A63B 24/0062* (2013.01); *A63B 24/0087* (2013.01); *A63B 71/0622* (2013.01);
(Continued)

(58) Field of Classification Search
CPC ............ A63B 24/0062; A63B 24/0087; A63B 71/0622; A63B 2220/806;
(Continued)

(56) References Cited

U.S. PATENT DOCUMENTS 6,007,459 A 12/1999 Burgess
9,011,293 B2 4/2015 Shavit et al.
(Continued)

FOREIGN PATENT DOCUMENTS

CN 114035683 A 2/2022
CN 114782945 A 7/2022
(Continued)

OTHER PUBLICATIONS

International Search Report and Written Opinion for corresponding International Application No. PCT/US19/67242 filed Dec. 18, 2019, dated Feb. 28, 2020, 15 pages.

*Primary Examiner* — Omkar A Deodhar
*Assistant Examiner* — Shauna-Kay N. Hall
(74) *Attorney, Agent, or Firm* — Leech Tishman Fuscaldo & Lampl, LLC

(57) ABSTRACT

A telehealth training system is provided which employs a three-dimensional camera programmed for capturing image data associated with an exercise program performed by a user. A computer-implemented body pose analysis and scoring module analyzes and scores body poses of the user while the user performs the exercise program. The analysis and scoring module may calculate scores in response to reference data related to at least one exercise prescribed for the user, and then compare processing results to the reference
(Continued)

data. A feedback module may be included in the system which is programmed for creating and animating an avatar in response to the processing results of the analysis and scoring module. In certain aspects, the analysis and scoring module may be programmed for using a voxel basis function (VBF) technique in connection with performing pose matching analysis in association with the user performing the exercise program.

27 Claims, 12 Drawing Sheets

(52) U.S. Cl.
CPC ............ *G06V 10/25* (2022.01); *G06V 40/103* (2022.01); *G06V 40/23* (2022.01); *G16H 20/30* (2018.01); *G16H 40/67* (2018.01); *A63B 2024/0096* (2013.01); *A63B 2071/0677* (2013.01); *A63B 2220/806* (2013.01)

(58) Field of Classification Search
CPC .... A63B 2024/0096; A63B 2071/0677; G16H 20/30; G16H 40/67; G06K 9/00369; G06K 9/3233; G06K 9/00342
See application file for complete search history.

(56) References Cited

U.S. PATENT DOCUMENTS

| | | | |
|---|---|---|---|
| 9,283,429 B2 | 3/2016 | Aragones et al. | |
| 9,302,170 B2 | 4/2016 | Balakrishnan et al. | |
| 9,694,241 B2 | 7/2017 | Balakrishnan et al. | |
| 9,747,722 B2 | 8/2017 | Adler et al. | |
| 9,875,664 B2 | 1/2018 | Dalal et al. | |
| 9,883,838 B2 | 2/2018 | Kaleal, Iii et al. | |
| 9,892,655 B2 | 2/2018 | Snow et al. | |
| 9,919,186 B2 | 3/2018 | Aragones et al. | |
| 9,977,874 B2 | 5/2018 | Aragones et al. | |
| 9,981,193 B2 | 5/2018 | Adams et al. | |
| 9,987,520 B2 | 6/2018 | Shavit et al. | |
| 2009/0042695 A1 | 2/2009 | Chien et al. | |
| 2010/0280418 A1 | 11/2010 | Klose | |
| 2012/0268372 A1 | 10/2012 | Park et al. | |
| 2013/0123667 A1 | 5/2013 | Komatireddy et al. | |
| 2013/0178960 A1 | 7/2013 | Sheehan et al. | |
| 2013/0252216 A1 | 9/2013 | Clavin et al. | |
| 2014/0172377 A1 | 6/2014 | Taubin et al. | |
| 2014/0270351 A1 | 9/2014 | Hoof et al. | |
| 2014/0287389 A1 | 9/2014 | Kallmann et al. | |
| 2016/0086500 A1 | 3/2016 | Kaleal, Iii | |
| 2017/0004631 A1 | 1/2017 | Yang | |
| 2017/0249401 A1 | 8/2017 | Eckart et al. | |
| 2017/0266491 A1* | 9/2017 | Rissanen | G09B 19/003 |
| 2018/0121728 A1 | 5/2018 | Wells et al. | |
| 2018/0130373 A1 | 5/2018 | Bernard-Paroly et al. | |
| 2018/0199861 A1 | 7/2018 | Ye et al. | |
| 2018/0228430 A1 | 8/2018 | Perez Marcos et al. | |
| 2018/0369637 A1 | 12/2018 | Hoang et al. | |
| 2022/0105389 A1* | 4/2022 | Lianides | A63B 24/0075 |

FOREIGN PATENT DOCUMENTS

| | | |
|---|---|---|
| CN | 114035683 B | 3/2024 |
| DE | 102022112008 A1 | 11/2023 |
| MX | 2021007514 A | 10/2021 |

* cited by examiner

REAL-TIME, FULLY INTERACTIVE, VIRTUAL SPORTS AND WELLNESS TRAINER AND PHYSIOTHERAPY SYSTEM

FIELD OF THE INVENTION

In various embodiments described herein, computer-implemented tools, techniques, devices, and technology are provided for a virtual sports and wellness trainer and physiotherapy system which can be used by practitioners to assist patients, trainees, and other subjects or users. In various embodiments, the invention relates generally to the fields of computer vision, artificial intelligence, and real-time animation.

BACKGROUND

In the world of physical therapy, rehabilitation, and fitness, improved tools are needed which can more effectively enhance exercise program compliance, patient exercise performance, and positive patient outcomes. For example, conventional physical therapy programs do not provide an enjoyable user experience, do not sufficiently promote patient compliance with participation, and do not provide useful feedback on the correct performance of exercises in the program. These deficiencies typically result in increased health care expenses, for example, while severely limiting the positive outcomes which otherwise might be realized by a patient who is properly performing and completing the exercise program.

Accordingly, computer-implemented tools, techniques, devices, and technology are needed that can empower physiotherapy practitioners to assist patients, trainees, and other users more effectively.

DESCRIPTION

Figure 1:
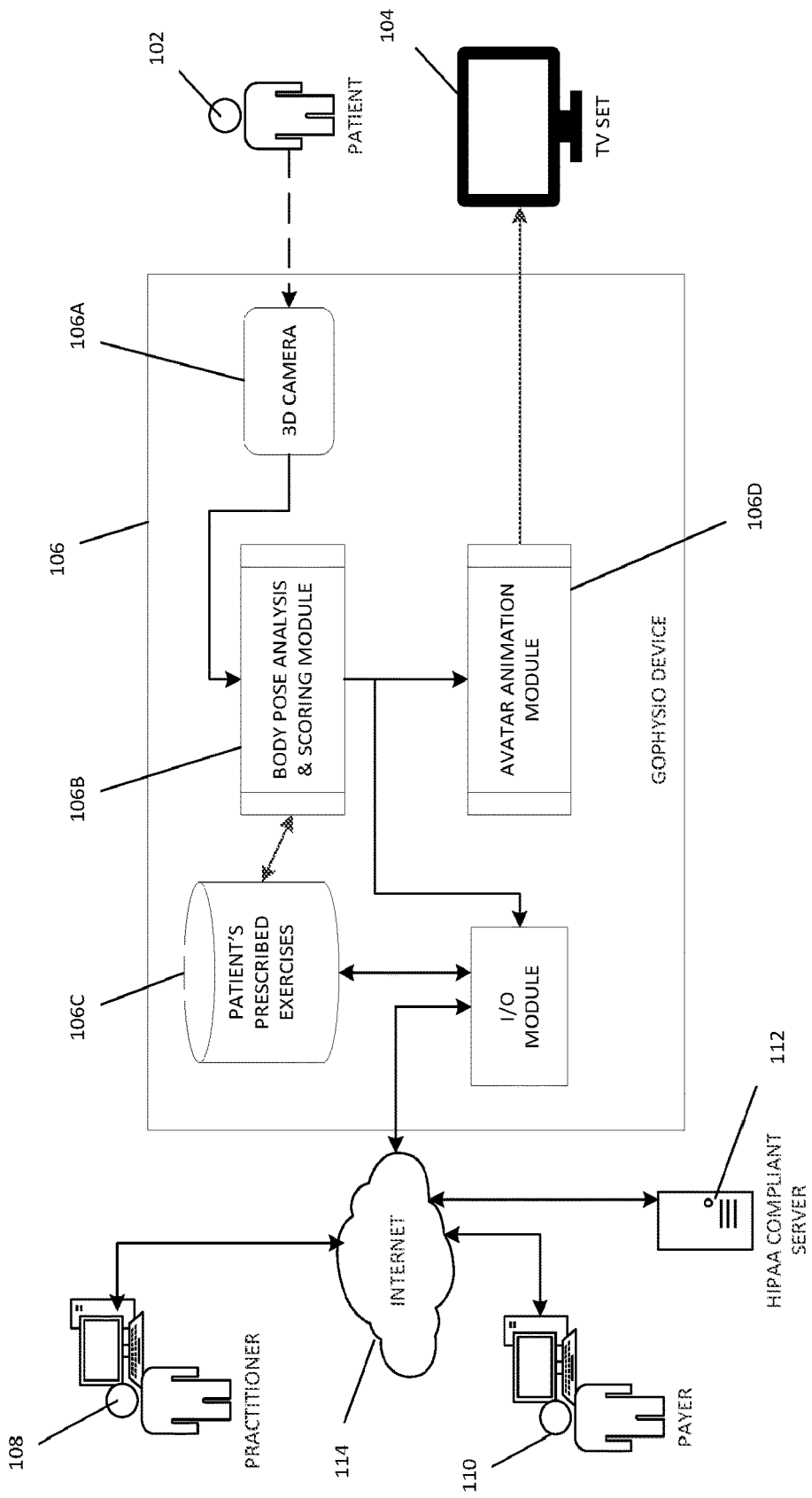
FIG. 1 schematically illustrates certain aspects of one example of a telehealth training system architecture and associated process flows in accordance with certain embodiments of the present invention.

The inventors have developed an advanced, intelligent system based on their enhanced motion capture and analysis technology. Embodiments of the invention described herein represent efficient tools for conducting physical therapy, rehabilitation, fitness and more. The invention can revolutionize physical therapy, rehabilitation and fitness performance by improving compliance with therapy programs and improving patient outcomes through an enjoyable interactive user experience.

The tools and systems described herein can capture motion, derive data and offer intelligent guidance while the user is submerged in a truly immersive experience. By analyzing the data using artificial intelligence techniques, the training device delivers improvements in the outcome of the rehabilitation or training process while ensuring compliance. On-screen avatars can demonstrate how to correctly perform prescribed exercises, while the patient receives corrections, encouragement and guidance. In one embodiment, a home-based, affordable automated system provides therapeutic guidance and assessment to home-bound patients or to those who do not have ready access to a clinic.

The training devices can more precisely capture and measure physical positions and movements. Based on scoring algorithms and empowered by AI algorithms, the devices may animate avatars that provide guidance, corrective feedback and encouragement to users. Captured data from patient sessions can then be uploaded to servers for further analysis and to communicate results and progress to the participant's practitioner and/or trainer. The device may be embodied as a small, light and portable plug & play unit that integrates a camera with a processing unit. In one example, a HIPPA-compliant cloud-based server can be employed to ensure safe and rapid interaction between practitioners and users.

Real-time corrective feedback can be generated and communicated based on accurate analysis of the person's positions and movements. Reliable physical assessments can be conducted based on an in-depth analysis of a person's musculoskeletal position and movements. The device can be configured to continue operating under extreme environmental and lighting conditions. In one embodiment, the computer system of the device cancels noise and background interference to ensure accurate measurements. Through executing its operatively associated algorithms, the device can compute positions and movements even when certain limbs of a patient, for example might be occluded from view. The device may include a camera equipped with optics and a built-in computer. The computer system of the device can capture an image of a person exercising at home, analyze it and then, through use of a set of algorithms and leveraging AI, estimate positions and movements with high accuracy and provide corrective feedback through an intelligent avatar.

In developing the solutions embodied by the various embodiments of the present invention which solve certain problems identified in the field of the invention, the inventors have recognized and were motivated by the following significant limitations in the prior art: the inability to accurately obtain depth data from a person exercising in the floor due to near-infrared reflections from the floor and objects around the person; the inability to estimate the exact three-dimensional skeleton representation of the person exercising when the person dresses in loose clothing and/or of material that absolves the near-infrared light generated by the depth camera; the inability to filter out background noise embedded with the signals produced by the depth camera, when is indiscernible from the true signals based on similar statistics structure; the inability to track body poses properly in environments rich with fixed objects like furniture, walls, etc.; the inability to properly track body motion when a second object moves within the field of view of the three-dimensional (3D) camera; the inability to properly track body motion when from certain angles the body is occluded by parts of itself; the lack of real-time feedback normally expected by a patient from a physical (i.e., not virtual) trainer or physiotherapist; and. the necessity to use expensive, high-performance computer processors.

The present disclosure describes examples of a fully interactive system for use as a virtual trainer or virtual physiotherapist which accurately assesses and measures exact body poses and motion in noisy and, at times, unstable video streams captured by a 3D (depth) camera. The system may use an avatar generated and animated in real-time, to communicate with the person exercising by providing visually and audible feedback by way of instructions, corrections, encouragement and other scripts, in a human-like fashion.

The present disclosure also describes certain embodiments of a gesture recognition set algorithm for estimating the position and movement of 20 specific bones, for example, that visually create a simplified skeleton. This skeleton can be compared and scored against a pre-set collection of poses and movements each with a variable threshold, which can be used to determine how to animate avatars and drive a speech module for corrective feedback purposes for the patient. Also, various embodiments of novel techniques are provided that permit a low to medium performance computer system and graphical processing unit to estimate a person's body poses and movements more accurately, to score them against pre-set poses and movements using adaptive thresholds, and then drive the action of an avatar by delivering animation and speech scripts.

In addition, the present disclosure describes examples of methods and apparatus for using a 3D camera to track subjects exercising while standing or laying in the floor which may be surrounded by multiple static objects. The 3D camera operates while the field of view may be exposed to high entropy noise caused by ground reflections and infrared interference, crossing elements (e.g., pet crossing), auto and hetero occlusion, and other challenges which conventional 3D cameras and devices cannot handle properly.

In one particular embodiment of the invention, a telehealth system and associated devices are provided which can be used by a person conducting a series of physical exercises prescribed by a physiotherapist and within a home-based or residential environment, for example. In this example, the embodiment of the device is a 3D camera with a low performance computer system and graphic processing subsystem that interacts with the person exercising through an avatar displayed in a television. The device guides, instructs, corrects and encourages the person exercising, as the device analyzes the person's poses and movements, and then compares them to the ideal poses and movement prescribed by the trainer or practitioner.

In certain embodiments, a system solution can be provided that performs correctly for patients of various sizes, exercising at different paces, standing at different angles with respect to the camera, and for other variations. The system employs improved algorithms to enable the skeletonizer to deal with issues related to camera optics, such as joint rotation estimates which diverge from the model as a function of distance and the angle of observation. This challenge required creation of a non-linear normalization process to promote keeping the exercise measurement and scoring results within acceptable tolerance levels. In one example, the person exercising is following exercises prescribed by a physiotherapist, who can modify the prescription, monitor progress, and communicate with his patient, through a software application hosted in a secure server, which may be a cloud-based server, for example.

The present invention represents a significant improvement over the prior art, which focuses on standing exercises only and does not provide real-time feedback by way of avatars. The present system is fully interactive through an avatar generated in real-time that shows the exact physical poses and movements prescribed, while delivering a visual and verbal feedback which mimics the way a typical trainer or physiotherapist would provide such feedback. Examples of this feedback include using scripted vocabulary and intonation that depend on the scoring, the type of errors, and also may involve showing past errors, so the feedback is made as realistic as possible.

Various embodiments of the present invention represent a significant improvement in the state of the art, because they permit use of a 3D camera, and low cost, low to medium performance central processing unit (CPU) and graphic processing unit (GPU) architecture to accurately measure and score subject body poses and movements. And these functions can be performed under high entropy noise conditions caused by lighting conditions, reflections, or objects obstructing the field of view, for example, among other noise conditions. In addition, various embodiments of the invention embody an intelligent, low-cost, small and portable, fully interactive, virtual physical therapy and rehabilitation system. The system, based on an accurate measurement of a person's position and movement, while standing or laying in the floor or a surface, provides instructions, corrections and encouragement through an avatar displayed to the patient in real-time.

The present invention may include a system comprised of an all-in-one small and portable apparatus powered by software, and potentially a server application hosted on the Internet cloud. Certain embodiments of the software and algorithms described herein are unique as they were designed to operate in a low-cost hardware architecture based in a processing unit with limited capabilities. The software and algorithms are nonetheless able to accurately capture, analyze, measure and score body poses and movements versus predetermined templates within environments which may present adverse lighting and reflective conditions, for example.

In various embodiments, the invention described herein provides tools, techniques, and technology for body pose and movement estimation using a low signal-to-noise data stream of depth images captured by a 3D camera, including high entropy noise, based in a real-time elimination of the noise using a combination of a time-series Markov, Bayesian or other non-statistical prediction methods. Accurate measurements of the body positions and movements are provided for people of various sizes, exercising at different paces, standing at different angles with respect to the camera, among other variables, by correcting the three-dimensional skeleton estimator for effects caused by camera optics, as a function of distance and the angle of observation. Software algorithms can be executed that may use simplified mathematical formulas, allowing measurement and scoring of distances between the positions and movements of the patient exercising and the prescribed positions and movements as set forth by the practitioner. This provides reliable feedback in the form of instructions, corrections and encouragement to the person exercising.

Effective algorithms that can operate in a low to medium performance CPU and GPU environment that can create, animate and display in front of the patient an avatar that acts and "talks" as a virtual physical therapist. The avatar can be programmed to give instructions, corrective suggestions, and encouragement in a realistic and professional manner.

Figure 2:
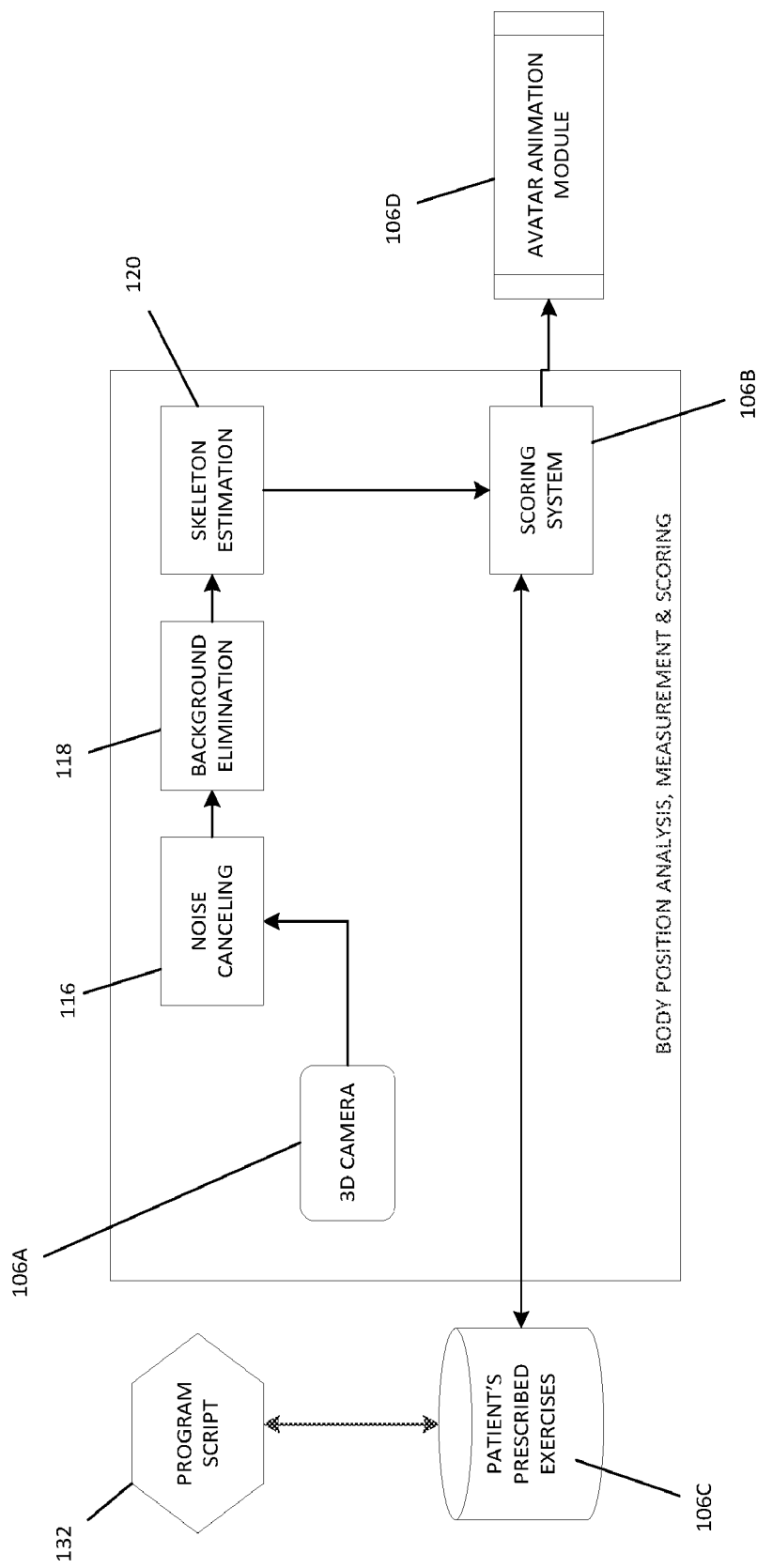
FIG. 2 schematically illustrates certain aspects of one example of a telehealth training system architecture and associated process flows in accordance with certain embodiments of the present invention.
Figure 3:
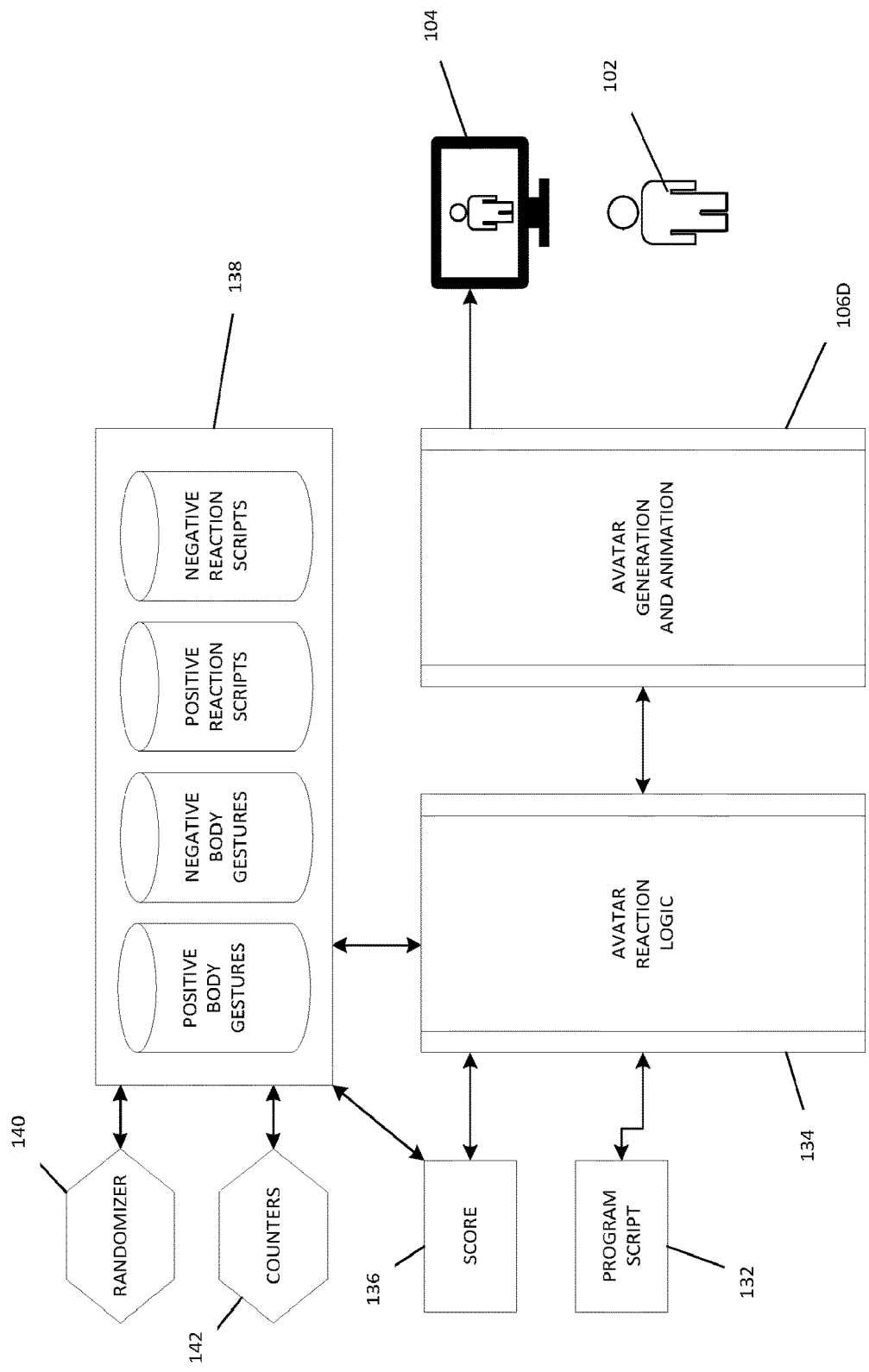
FIG. 3 schematically illustrates certain aspects of one example of a telehealth training system architecture and associated process flows in accordance with certain embodiments of the present invention.

FIGS. 1 through 3 collectively depict an example of a telehealth training system architecture and associated process flows connected with certain embodiments of the present invention. In this example, a patient 102 is exercising in front of a screen display 104 (e.g., television). The patient 102 is positioned to interact with a training device 106 which is operatively interfaced to display information on the screen display 104, as shown. The device 106 can be embodied as a small, portable device for home-based telehealth activities, such as engaging in physical therapy sessions. In the example shown, the device 106 includes a three-dimensional camera 106A programmed for capturing image data associated with the patient 102 exercising, and a processing unit that initially estimates body poses of the patient 102 with a body pose analysis and scoring module 106B. The training device 106 calculates the score utilizing, as a reference, data related to the prescribed exercises stored in a suitable data storage medium or media 106C. The module 106B also communicates with a feedback module 106D programmed for creating and animating an avatar. It can be seen that the training device 106 also communicates with practitioners 108 and, in this particular case, with methods and other third parties 110, via a server 112 hosted in a cloud-based computing environment 114, for example.

In certain aspects, FIG. 2 illustrates an example of a software process related to body position analysis, measurement and scoring executed in association with the training device 106. As shown, a noisy (i.e., in the context of a "noisy" signal-to-noise ratio) video stream delivered by the 3D camera 106A can be processed by a noise cancelling module 116 before all static background such as fixtures and also moving objects in the field of view such as pets, for example, are eliminated or reduced by a background elimination module 118. The resulting data may be processed by a skeleton estimation module 120, which is programmed to use the data clean of noise and foreign objects to estimate accurately the body poses and movements. Data associated with these estimates may be scored by the scoring module 106B, which is programmed to compare the body poses and motion as performed by the patient against the ones prescribed by the practitioner 108. The results of the scoring module 106B can be used by the avatar animation module 106D to generate the kind of feedback to be communicated to the user 102 by the avatar. Such feedback might be words of encouragement, visually demonstrating correct motions, new instructions, audible alarms, and/or many other kinds of feedback which help the patient 102 to comply with the therapy program.

FIG. 3 depicts an example of a software process related to the generation and animation of the avatar which is one method which the system can use to communicate with the person 102. In various embodiments, a program script 132 or another set of computer-readable instructions, can be used to direct the tasks and functions of the training system and/or the device 106, including determining what content is communicated to the user 102. For example, the program script 132 may direct which prescribed exercises should be presented to the patient 102. In another aspect, at various stages of execution of the program script 132, an avatar reaction logic module 134 can be programmed to analyze scores 136 (perhaps generated by the analysis and scoring module 106B) to decide what kind of feedback to communicate. The training system can access one or more databases 138 which store a number of positive and negative scripts associated with communicating multiple avatar movements and voice messages to the patient 102. In certain embodiments, the positive and negative scripts may be randomized by a randomizer 140 and/or may be generated in response to one or more counters 142 to promote the avatar "moving" and "talking" in a non-repetitive way, for example, which presents a more realistic visual experience for the patient 102. As a result of this mechanism, the avatar reacts differently and relevantly when the person exercising has to be corrected or encouraged.

Figure 4:
FIG. 4 includes a screen display illustrating one example of a device scanning the exercise program environment.
Figure 5B:
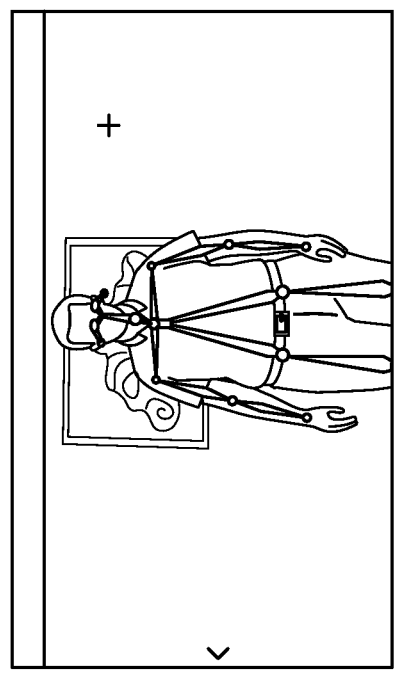
FIGS. 5A and 5B include screen displays illustrating one example of how depth information of the user can be post-processed with three-dimensional segmentation techniques.
Figure 5A:
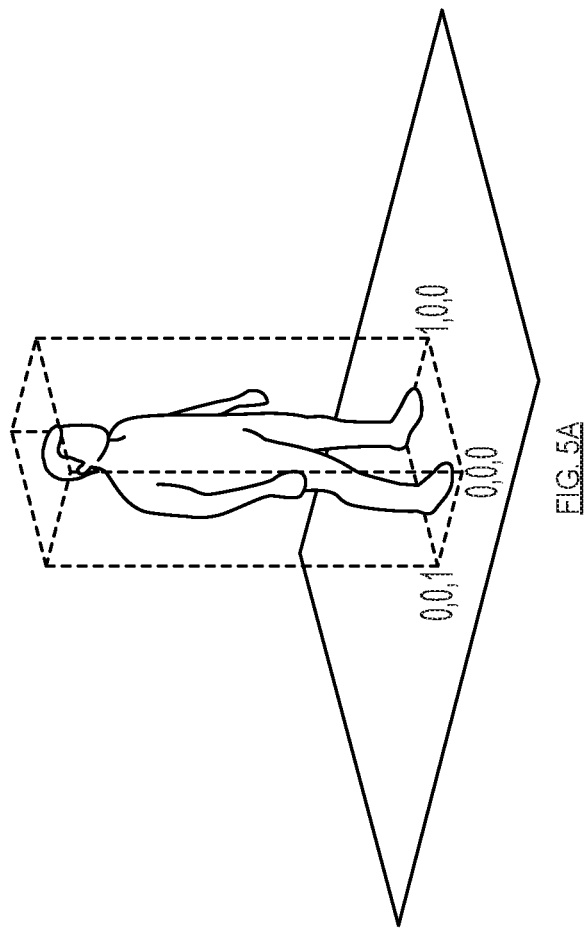
Figure 6A:
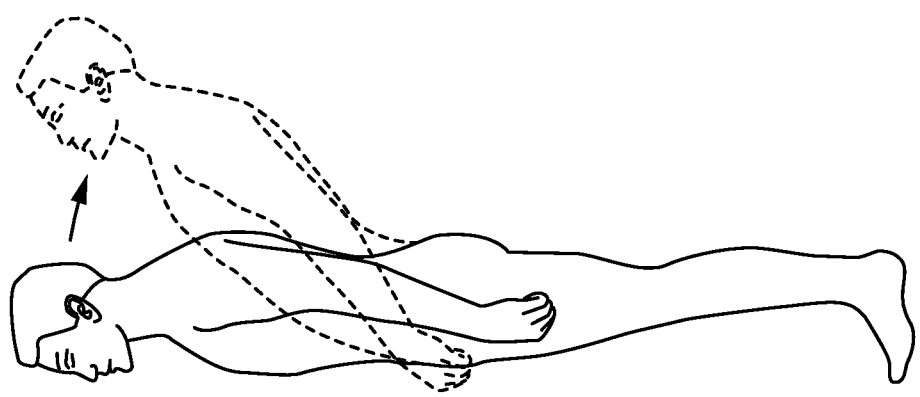
FIGS. 6A-6D illustrate an example of how a piecewise continuous basis function (PCBF) technique can be employed in connection with body pose analysis.
Figure 6C:
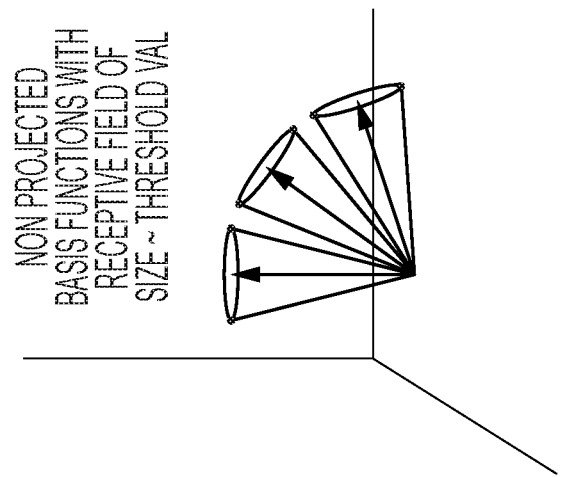
Figure 6B:
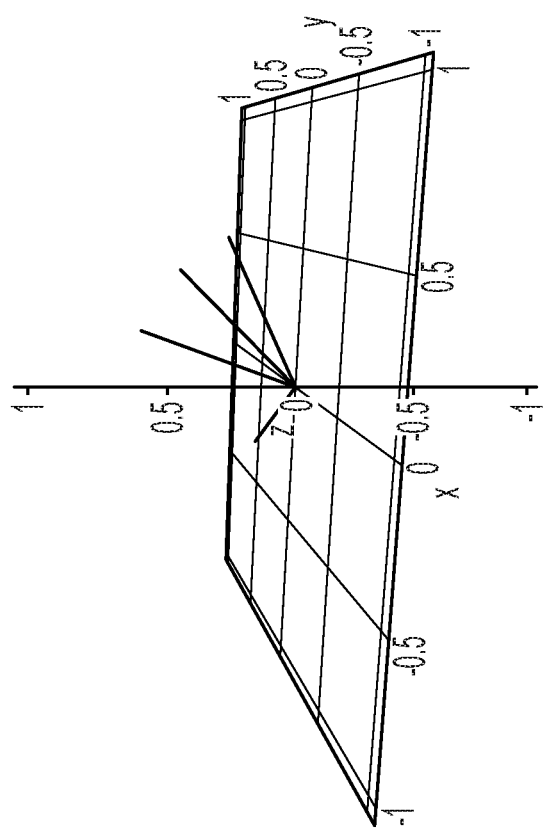
Figure 6D:
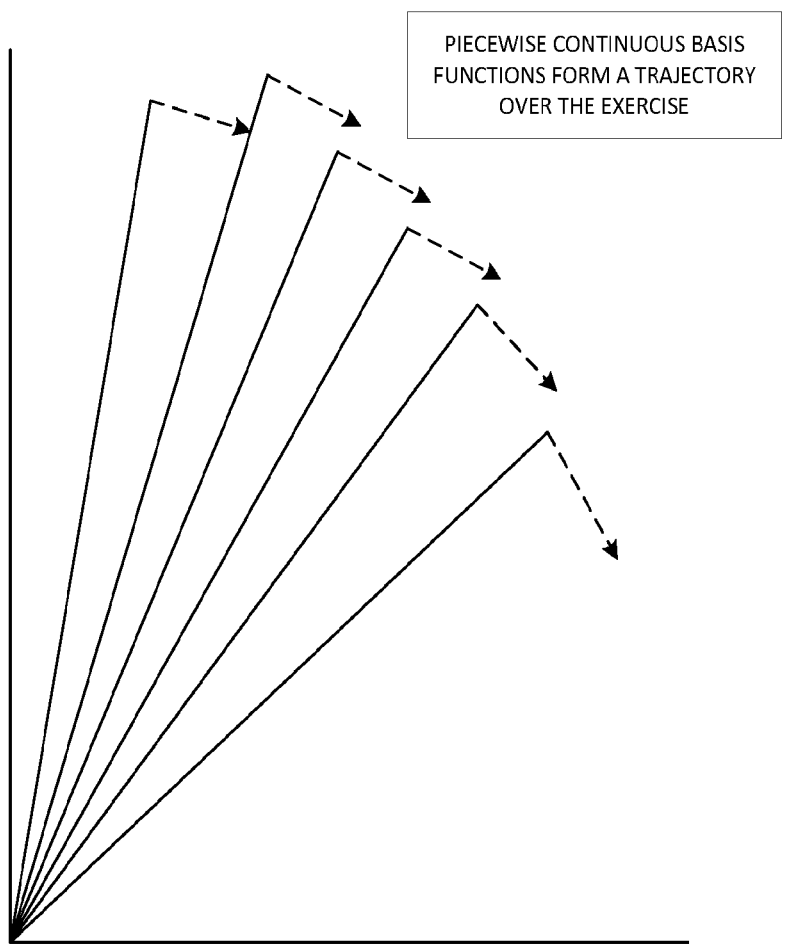

In one example of certain embodiments of the invention, and with reference to the example of a screen display shown in FIG. 4, the system can be programmed to scan the exercise program environment to learn the background. After an initial scan of the environment, the device measures depth information from the scene without the user 102 present. It then uses this as a baseline to determine which subsequent depth information belongs to the user 102. As shown in FIGS. 5A and 5B, the depth information of the user 102 can be post-processed with three-dimensional segmentation techniques in order to separate the information into a series of oriented parts. These parts correspond to the estimates of each body part in the skeleton. This is one example of the skeleton estimation module 120 and its associated processing as described above.

Depending on whether skeleton information is available, one or more different techniques can be used for pose matching analysis. With reference to FIGS. 6A-6D, a piecewise continuous basis function (PCBF) technique can be employed, for example. For each exercise, features in the skeleton/body pose estimate of the user can be selected that are most statistically relevant. These are compared to the movements of the avatar to assess and score the user's movement. The number of vector samples required can be determined, along with their associated projection coefficients. The system can project onto the direction of movement of the source avatar, such that there is sufficient coverage over the exercise. The avatar source signal and the user signal can be sampled, evaluating proximity using projected inner product distance between movement vectors to determine a frame score for the user, and progression through the exercise, as follows: frame_score(t)=x(t)·y(t)=$\|x(t)\|\|y(t)\|\cos(\alpha)$. Progression through the exercise can then be modeled as a traversal through an activation sequence of these filters.

Figure 7A:
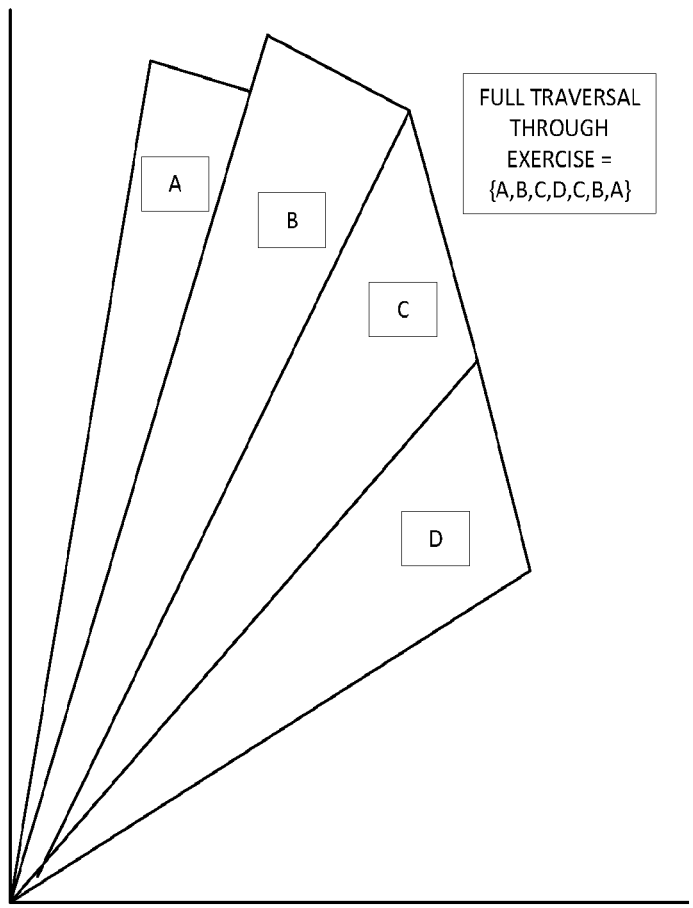
FIGS. 7A-7C illustrate an example of a voxel basis function (VBF) technique which can be used for body pose analysis and matching.
Figure 7B:
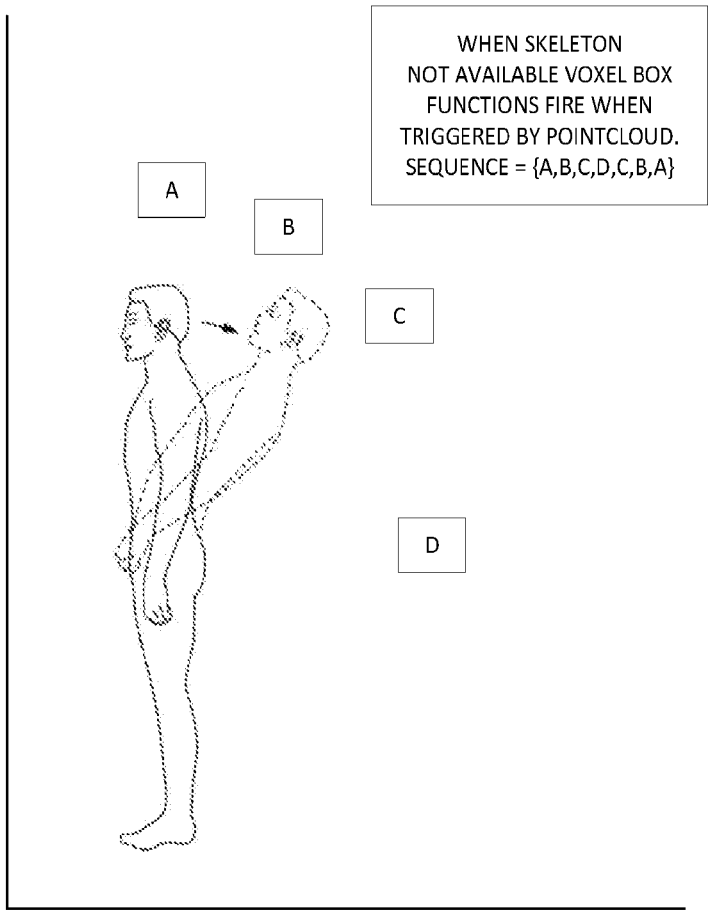
Figure 7C:
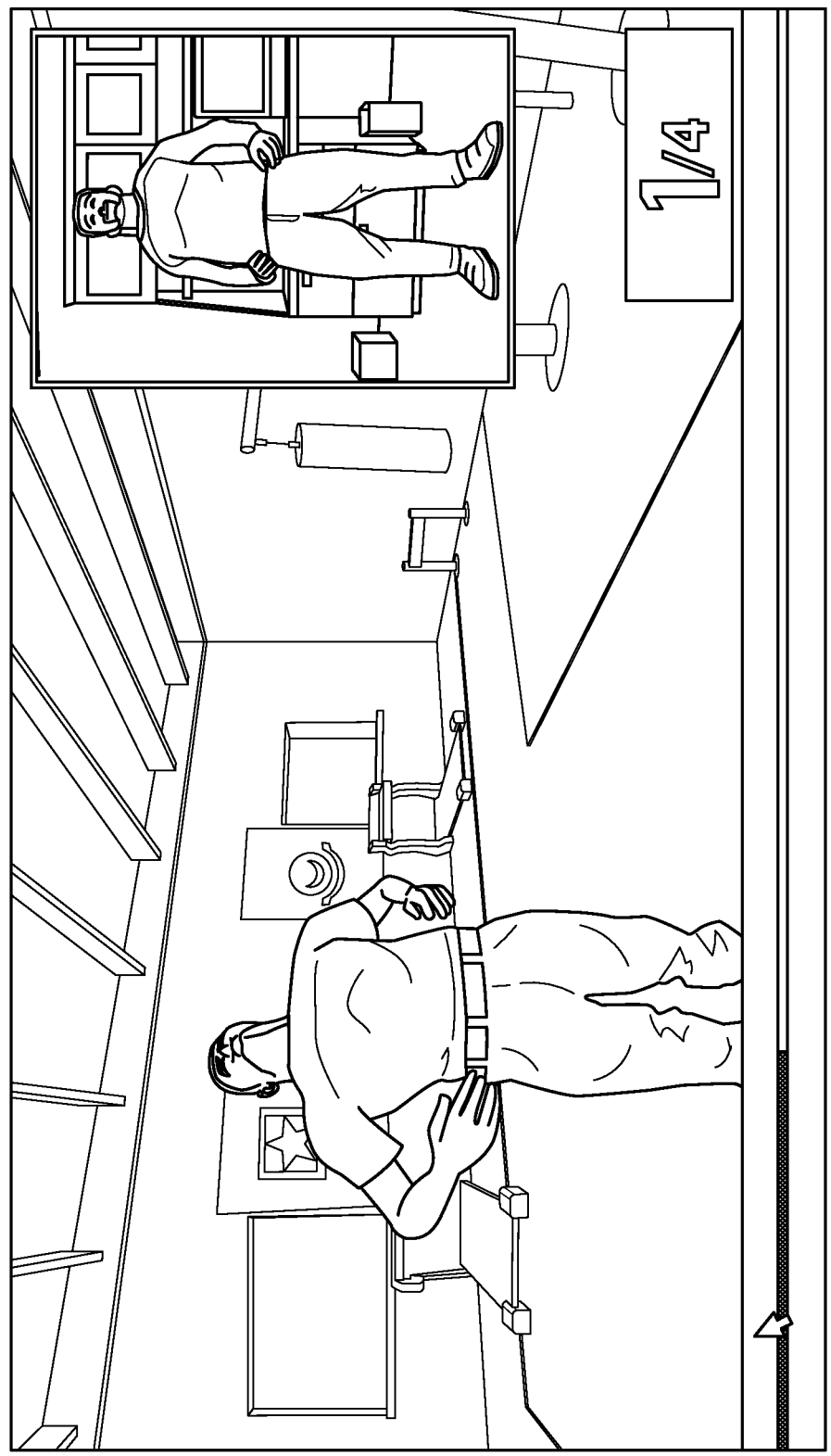

With reference to FIGS. 7A-7C, another example of a technique which can be used for pose matching analysis is a voxel basis function (VBF) technique. In certain situations where skeleton information might not be available, the same heuristic applies, although instead of modeling the feature trajectory with axis function vectors, a sequence of axis-aligned bounding boxes can be used. As described above, a sequence of bounding boxes may be used to track progression of the user 102 through the exercise.

Figure 8:
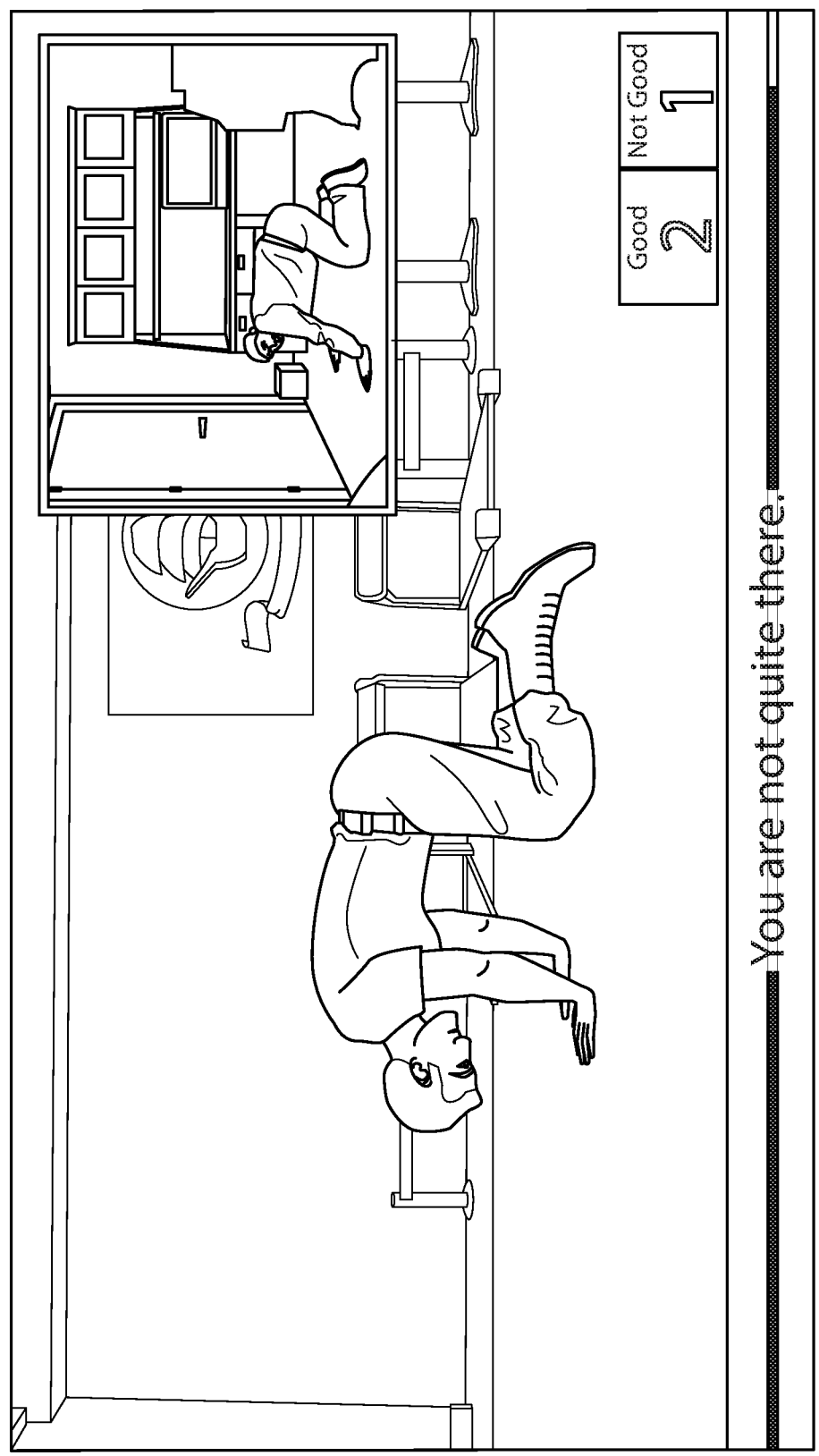
FIG. 8 includes a screen display illustrating examples of how feedback can be communicated to a user.

At the next stage, time invariant frame scores for the user 102 compared to the avatar signal can be summed to determine an exercise repetition score of the user 102. After which the avatar can be adjusted and animated to provide corrective feedback, praise or encouragement to the user 102. In the example of FIG. 8, the system communicates "You are not quite there" to the patient 102.

Once the exercise repetition scores are tallied, the system moves to the next exercise in the prescribed set and proceeds to score each repetition through the frame score heuristic described above. The system then uploads the score information and motion data to the server, and the data can be anonymized to conceal identifying information of the user 102 for data privacy purposes.

It can be appreciated by those skilled in the art that embodiments of the invention provide a new method and process for generating and estimating a simplified 3D skeleton of a person standing or laying on the ground, from a noisy stream of video data generated by 3D cameras.

In various embodiments, the invention provides a framework to facilitate high-frame-rate body motion tracking using Android based, low cost hardware architecture. A background elimination framework can provide focus on only the individual in the field of view, regardless of stationary or moving occluding objects in the field of view (e.g. a crossing dog, cat). Computer-based methods can be used to post-process skeletal information to compensate for characteristically high entropy noise due to environmental reflections person's size, reflection of various materials in the background, occlusion, and auto-occlusion.

In certain aspects, the invention addresses how to use auto-convolutional like network methods, to build a support vector machine that tracks statically relevant joints for pose recognition, analysis and scoring. The inventors have developed a time invariant multi-state inner product technique for scoring maximally effective sub manifold of input space, with adaptive machine learning to track user progress and adjust tracking difficulty and sensitivity. The PCBF technique described herein provides numerical methods to choose maximally relevant features across all poses, from which a piecewise continuous trajectory is defined through a subspace of the bones in the source signal. The state of a bone trajectory is defined as a set of eigenpairs for the trajectory vector and threshold values.

The inventors have designed simpler, more elegant algorithms and mathematics to score a chosen subset of bone trajectory vectors using projections of the inner product onto sub-spaces that minimize reconstruction error. As each subsection (state) is matched (through evaluating reconstruction error), time series progress can be estimated through a Markov process, for example, a stochastic process for which the conditional probability distribution of future states depends only on the current state (and not on past states).

The inventors had identified ways to minimize computational requirement for the use of kernel functions for support of vector machines. A new way has been developed to project bone trajectories into inner product measurement scales in the R3 field, which naturally distributes drift in reconstruction error across the local right, forward and up basis vectors which can replace or supplement the standard Euclidean, Hamiltonian or second order difference heuristics techniques in the prior art. The inventors have also created a new technique for selecting subspace projections of motion data onto the principal axes to filter orthogonal, noisy, random and semi-random user signals.

In other aspects, a machine learning method can be used that adapts difficulty and sensitivity thresholds by adjusting the eigenvector value pair based on range of motion and past performance. In the area of adaptive learning, a modified Kalman filter can be implemented in order to predict the second and third order statistics of the eigenpair values based on user performance as well as a priori knowledge of human kinematic movement patterns. Also, by projecting the eigenpair onto a subspace, reconstruction error is minimized, dimensionality reduction and fast learning convergence can be achieved.

Since normal skeleton tracking was not always possible in the prior art, the VBF technique was developed that is optimal for ground exercises, or standing exercises where skeleton information is unavailable, or for exercises where skeletal tracking is not otherwise available or desired. In this model, exercise poses scored through the Markov process through the covariance field of VBF activation functions, where the VBF kernel function is an axis-aligned bounding box that propagates signal magnitude when depth information is bound within its constraints, and gates the signal otherwise. The covariance field of VBF per hidden state enables per feature scoring by activating when motion vectors are sampled while filtering orthogonal and noisy samples concurrently.

Given a non-skeletonized mesh data representation of a user performing exercises, a fast technique can be implemented for a minimal skeleton for ground exercises, appropriate for low cost computer hardware, for example. The concept of VBF mentioned above initially applied to the mesh, generating an axis-aligned bounding box spanning convex hull. The top-most surface of the hull can be filtered and separated using spatial filtering techniques, for example. This surface can then be subdivided into end points and middle pose indices. These indices may then be used as the center of mass for bone estimates of the feet, head, and hips/midpoint, or other body parts of a user. Certain algorithms may be based on other techniques whereby each pixel is seen as a completely individual unit, with two separate timelines for correct and incorrect behavior. In one case, for every iteration a unit is processed the tracking becomes better defined to the current input of the 3D depth camera. The process of the algorithm may not have a set time, but measures the possible duration while in machine learning mode.

The inventors have created a way for establishing a connection from a home device to a practitioner via an information network, and methods for transmitting a user's physiotherapeutic pain condition from the user to the practitioner. The training system provides a method to modify prescribed exercises by practitioner; to transmit a selected series of video files containing the images of the user's movements when exercising; and to provide corrective feedback to the user by way of an animated avatar that uses full body animation and text to speech to communicate. The training system can also be configured to change threshold used for scoring determination, and/or to compare the difference between two different streams of data related to 3D skeleton models, when they represent movements of people of different sizes moving at different paces, for example.

Those skilled in the art can appreciate that numerous advantages and benefits are offered by one or more embodiments of the present invention:

To analyze accurately the exact position and movement of the patient under several environmental conditions, including but not limited to, floor exercises, in an environment rich in fluctuating infrared (IR) reflections, that people or animals cross the camera's field of view, when the patient is dressed in loose clothing, and/or obstacles which absorb the infrared light used by 3D cameras, etc.

To provide new ways for body pose estimation, which is a high order multi-dimensional approximation problem that uses a new kind of skeletonizer (algorithms that estimate the exact skeleton of a person) as the stream of images from depth cameras includes high entropy noise, background data and other elements with the signal that can be eliminated using time series, Markov, Bayesian or other non-statistical prediction methods.

To provide a system solution that performs correctly for patients of various sizes, exercising at different paces, standing in different angles with respect to the camera, etc., or other variables. This challenge is addressed by an improved skeletonizer programmed to deal with issues related to camera optics, which may cause joint rotation estimates to diverge from the model as a function of distance and the angle of observation. This is addressed by creating a non-linear normalization process to promote exercise measurement and scoring results within acceptable tolerance levels.

To provide software-based algorithms that allow measurement of the distance between the estimated position and movement of the skeleton of the patient exercising, with a predetermined template of the same, so as to provide accurate feedback to the person exercising.

To perform the functions, features, and tasks described herein, in real-time, using a low-cost hardware driven by Android, for example, among other similar operating systems, while still maintaining a minimum frame-rate of 30 frames per second, for example.

To execute algorithms that allow, in real-time, create, animate and display an avatar that acts as a virtual physical therapist, giving instructions, corrections and encouragement in a visually realistic and professional manner.

To create a risk-adverse system architecture that is secure, protects privacy, such that its users cannot be located geographically, if not desired.

To provide feedback to the person exercising by way of an avatar that is presented in human-like fashion and is realistic.

Other advantages and benefits of the present invention that become apparent or obvious from the detailed description or illustrations contained herein are within the scope of the present invention.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, configurations, data definitions, or process flows described herein are necessarily intended to limit the scope of the invention, unless such aspects are specifically included in the claims.

Any element expressed herein as a means for performing a specified function is intended to encompass any way of performing that function including, for example, a combination of elements that performs that function. Furthermore, the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, various models or platforms can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth. Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described herein above may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. Wireless communications described herein may be conducted with Wi-Fi and Bluetooth enabled networks and devices, among other types of suitable wireless communication protocols. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the wireless device to the network. The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a processor or application specific processor.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. Discrete components and features may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by hardware as discussed above, as an alternative the same may also be embodied in dedicated hardware or a combination of software/hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc.

The flow charts and methods described herein show the functionality and operation of various implementations. If embodied in software, each block, step, or action may represent a module, segment, or portion of code that comprises program instructions to implement the specified logical functions. The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical functions.

Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment. The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as" or "for example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as described and claimed herein.

What is claimed is:

1. A telehealth training system comprising:
   a three-dimensional camera programmed for capturing image data associated with an exercise program performed by a user;
   a computer-implemented body pose analysis and scoring module programmed for analyzing and scoring body poses of the user while the user performs the exercise program;
   the analysis and scoring module programmed for calculating a score in response to:
      reference data related to at least one exercise prescribed for the user, and
      comparing processing results of the analysis and scoring module to the reference data;
   a feedback module programmed for creating and animating an avatar in response to the processing results of the analysis and scoring module; and,
   the analysis and scoring module programmed for using a voxel basis function (VBF) technique in connection with performing pose matching analysis in association with the user performing the exercise program.

2. The system of claim 1, further comprising a module programmed for communicating at least a portion of the processing results of the analysis and scoring module to a data storage medium associated with at least one practitioner.

3. The system of claim 1, further comprising a module programmed for communicating at least a portion of the processing results of the analysis and scoring module to a data storage medium associated with at least one payor.

4. The system of claim 1, wherein the three-dimensional camera is operatively associated with at least one screen display located in an environment where the user performs the exercise program.

5. The system of claim 1, further comprising a noise cancelling module programmed for reducing signal noise contained in a data stream captured by the three-dimensional camera.

6. The system of claim 1, further comprising a background elimination module programmed for removing from image data captured by the three-dimensional camera at least one fixture in a field of view of the three-dimensional camera.

7. The system of claim 1, further comprising a background elimination module programmed for removing from image data captured by the three-dimensional camera at least one moving object in a field of view of the three-dimensional camera.

8. The system of claim 1, further comprising a skeleton estimation module programmed for generating at least one skeleton model for the user.

9. The system of claim 1, wherein the feedback module is further programmed for communicating visual or audible encouragement to the user in response to the user performing the exercise program.

10. The system of claim 1, further comprising the feedback module programmed for communicating at least one avatar movement or voice message in association with a positive script or a negative script.

11. The system of claim 10, further comprising the feedback module programmed for using a randomizer for randomizing at least one script to promote the avatar moving or talking in a non-repetitive way.

12. The system of claim 1, further comprising the analysis and scoring module programmed for using a piecewise continuous basis function (PCBF) technique in connection with the pose matching analysis.

13. The system of claim 1, further comprising the analysis and scoring module programmed for using the voxel basis function (VBF) technique when skeleton model information is not available.

14. The system of claim 13, further comprising the analysis and scoring module programmed for using a sequence of axis-aligned bounding boxes to track progression of the user through the exercise program.

15. A telehealth training method comprising:
   capturing, by a three-dimensional camera, image data associated with an exercise program performed by a user;

analyzing, by an analysis and scoring module, body poses of the user while the user performs the exercise program;

calculating a score, by the analysis and scoring module, in response to:
- reference data related to at least one exercise prescribed for the user, and
- comparing processing results of the analysis and scoring module to the reference data;

creating and animating an avatar, by an avatar animation module, in response to the processing results of the analysis and scoring module; and using a voxel basis function (VBF) technique in connection with performing the body pose analysis in association with the user performing the exercise program.

16. The method of claim 15, further comprising communicating at least a portion of the processing results of the analysis and scoring module to a data storage medium associated with at least one practitioner.

17. The method of claim 15, further comprising communicating at least a portion of the processing results of the analysis and scoring module to a data storage medium associated with at least one payor.

18. The method of claim 15, further comprising using a noise canceling module for reducing signal noise contained in a data stream captured by the three-dimensional camera.

19. The method of claim 15, further comprising using a background elimination module for removing from image data captured by the three-dimensional camera at least one fixture in a field of view of the three-dimensional camera.

20. The method of claim 15, further comprising using a background elimination module for removing from image data captured by the three-dimensional camera at least one moving object in a field of view of the three-dimensional camera.

21. The method of claim 15, further comprising using a skeleton estimation module for generating at least one skeleton model for the user.

22. The method of claim 15, further comprising communicating visual or audible encouragement to the user in response to the user performing the exercise program.

23. The method of claim 15, further comprising communicating at least one avatar movement or voice message in association with a positive script or a negative script.

24. The method of claim 23, further comprising using a randomizer for randomizing at least one script to promote the avatar moving or talking in a non-repetitive way.

25. The method of claim 15, further comprising using a piecewise continuous basis function (PCBF) technique in connection with the pose matching analysis.

26. The method of claim 15, further comprising using the voxel basis function (VBF) technique when skeleton model information is not available.

27. The method of claim 26, further comprising using a sequence of axis-aligned bounding boxes to track progression of the user through the exercise program.

* * * * *